(12) United States Patent
Sakamoto

(10) Patent No.: US 6,787,317 B1
(45) Date of Patent: Sep. 7, 2004

(54) METHOD OF IDENTIFYING MISSING DOMAINS IN RECEPTORS

(75) Inventor: Kenji Sakamoto, 25, Aza Kourokuzawa, Memeki, Yuuwa-machi, Kawabe-gun, Akita 010-1233 (JP)

(73) Assignee: Kenji Sakamoto, Akita (JP)

( * ) Notice: Subject to any disclaimer, the term of this patent is extended or adjusted under 35 U.S.C. 154(b) by 0 days.

(21) Appl. No.: 09/269,703

(22) PCT Filed: Oct. 1, 1997

(86) PCT No.: PCT/JP97/03499

§ 371 (c)(1), (2), (4) Date: Feb. 2, 2000

(87) PCT Pub. No.: WO98/14479

PCT Pub. Date: Apr. 9, 1998

(30) Foreign Application Priority Data

Oct. 2, 1996 (JP) .............................................. 8/281421

(51) Int. Cl.[7] ............................................ G01N 33/567
(52) U.S. Cl. ..................... 435/7.1; 435/7.2; 435/7.21; 436/501; 530/300
(58) Field of Search ........................ 435/7.1, 7.2, 7.21; 436/501; 530/300, 303, 307, 308, 311, 326

(56) References Cited

FOREIGN PATENT DOCUMENTS

WO       WO 93/10149    *  5/1993    ........... C01K/13/00

OTHER PUBLICATIONS

Ralf B. Nehring et al., "Aspartic Acid Residue 124 In The Third Transmembrane Domain Of The Somatostatin Receptor Subtype 3 Is Essential For Somatostatin–14 Binding", DNA and Cell Biol., 14 (11) (1995) pp. 939–944, 1995.

Si Lok et al., "The Human Glucagons Receptor Encoding Gene: Structure, cDNA Sequence and Chromosomal Localization", Gene 140 (1994) pp. 203–209.

Sandrine Gremlich et al., "Cloning, Functional Expression, And Chromosomal Localization Of The Human Pancreatic Islet Glucose–Dependent Insulinotropic Polypeptide Receptor", Diabetese, vol. 44, Oct. 1995.

Ii Song et al., "The Human Gastrin/Cholecystokinin Type B Receptor Gene: Alternative Splice Donor Site In Exon 4 Generates Two Variant mRNAs", Proc. Natl. Acad. Sci. USA vol. 90, pp. 9085–9089, Oct. 1993.

Mitsuhiro Ito et al., "Functional Characterization Of Two Cholecystokinin–B/Gastrin Receptor Isoforms: A Preferential Splice Donor Site In The Human Receptor Gene", Cell Growth & Differentiation, vol. 5, pp. 1127–1135, Oct. 1994.

Terry Reisine et al., "Splice Variant Of The Somatostatin Receptor 2 Subtype, Somatostatin Receptor 2B, Couples To Adenylyl Cyclase", Molecular Pharmacology, vol. 44, pp. 1008–1015, Aug. 1993.

* cited by examiner

Primary Examiner—John Ulm
(74) Attorney, Agent, or Firm—Brooks Kushman P.C.

(57) ABSTRACT

A method for searching, with a predetermined predictability and more ease, for new physiologically active substances is disclosed. In one method for searching for physiologically active substance according to the present invention, amino acid sequences of receptors having two or more sizes for identical receptors are identified, wherein a substance or cell having a functional antagonism is a receptor of a substance present in human body, or wherein a cell or substance having a functional antagonism to cells on which a certain substance causes some effects is a receptor of the substance present in human body, and it is identified which domain in the receptor having a longer size is missing in the receptor having a shorter size.

2 Claims, No Drawings

SEQUENCE LISTING

<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Lys Leu Thr Thr Ile Phe Pro Leu Asn Trp Lys Tyr Arg Lys Ala Leu
1               5                   10                  15

<210> SEQ ID NO 2
<211> LENGTH: 27
<212> TYPE: PRT
<213> ORGANISM: Rattus norvegicus

<400> SEQUENCE: 2

Gly Asn Gly Val Val Ser Ala Trp Glu Ala Glu Gly Ala Lys Ser Gly
1               5                   10                  15

Ser Gly Leu Thr Arg Ala Tyr Thr His Val Pro
            20                  25

<210> SEQ ID NO 3
<211> LENGTH: 12
<212> TYPE: PRT
<213> ORGANISM: Rattus norvegicus

<400> SEQUENCE: 3

Pro Ser Cys Gln Trp Val Gln Ala Pro Ala Cys Gln
1               5                   10

US 6,787,317 B1

METHOD OF IDENTIFYING MISSING DOMAINS IN RECEPTORS

This application is a 371 of PCT/JP97/03499 Oct. 1, 1997.

BACKGROUND OF THE INVENTION

1. Field of the Invention

The present invention relates to a method for searching for a variety of new physiologically active substances and producing the same.

2. Background Art

Physiologically active substances of unknown types have been searched, heretofore, by analyzing substances present in body fluids or tissues, and identifying and separating new substances therefrom to determine the physiological activities of said substances.

The prior art method as described above comprises the steps of analyzing components in living organisms, searching and isolating new substances, and identifying the physiological activities thereof. It is obvious, however, that there exist an extremely large number of substances within a living organism, and many physiologically active substances are often present at very low concentrations, thus making it difficult to isolate new substances. Furthermore, because living organisms perform a number of physiological activities, it may also be difficult to identify the physiological activities of a newly isolate substance. As can be appreciated from the above discussion, the prior art methods render it difficult to search and isolate new physiologically active substances.

SUMMARY OF THE INVENTION

One aspect of the present invention is to provide a method for searching, with more efficiency and a certain degree of predictability, new physiologically active substances.

The inventor of the present invention found that in the case of a receptor satisfying the following condition below, either X or Y, and also having one or more variants in size because of alternative splicing or post-translational modification, the amino acid sequence of the missing portion, i.e., the spliced portion or the portion inserted or added, has a physiological meaning. Condition X is the condition where there is in the body a substance or cell having a functional antagonism against a substance A which is a ligand of a receptor. Condition Y is the condition where there is in the body a substance or cell having a functional antagonism against a cell which expresses the receptor whose ligand being a substance A. For example, calcitonin may be bound to a calcitonin receptor present on osteoclasts to suppress the deossification effected by the osteoclasts, while there are osteoblasts that have functional antagonism against the osteoclasts. Regarding calcitonin receptors, there are already reported the amino acid sequence thereof, but there are reported two or more different types having different sizes. The inventor of the present invention has predicted that, in case of calcitonin receptors of such types having two or more sizes, one domain in the receptor of longer size is spliced thereby creating the receptor of shorter size, and that said spliced domain may cause effects on osteoblasts having effects antagonistic to the effects of osteoclasts on which calcitonin causes effects. Upon examination of the spliced domain after chemically synthesizing the domain, it was confirmed that this new peptide promotes osteogenesis by binding to receptors on the osteoblasts.

Such confirmation as above showed the correctness of the foregoing prediction made by the inventor of the present invention and the present invention was made.

In another words, the present invention provides a method for searching physiological active substances, the method comprising the steps of identifying an amino acid sequence of receptors which have two or more sizes when the receptors are functionally identical to each other, the receptor being a receptor of a substance when there is present in human body a substance or cell which have a functional antagonism, or the receptor being a receptor of substance when there is present in human body a cell or substance which have functional antagonism to cells on which said substance causes some effects, and determining which domain in the receptor of longer size is missing in the receptor of shorter size. The present invention also provides a method for producing physiologically active peptides, the method comprising the step of producing the missing domain, or the derivative thereof, identified by the method of present invention as described above.

One aspect of the present invention provides for the first time a method for searching, with efficiency and a certain degree of predictability, for new physiologically active substances. According to another aspect of the present invention, new physiologically active substances may be identified by analyzing receptors of substances associated with functional antagonism, thereby eliminating the necessity of isolating, as before in the prior arts, physiologically active substances present in a small quantity in a sample of human body which includes an extremely large number of components. Furthermore, because the physiological activity of the identified physiologically active substance is associated with said functional antagonism, it may be much easier than before to identify the physiological activities thereof. Therefore, according to one method of the present invention, it is made possible to identify new physiologically active substances in much more efficient way than before.

THE BEST MODE FOR CARRYING OUT THE INVENTION

According to one method of the present invention, focus is made on receptors, the receptor being a receptor of a substance when there is present in human body a substance or cell which have a functional antagonism, or the receptor being a receptor of substance A when there is present in human body a cell or substance which have a functional antagonism to cells on which the substance A causes some effects. The functional antagonism is a fundamental function for the homeostasis in human body and there are a large number of substances or cells having mutual antagonisms within human body. Examples of receptors, the receptor being a receptor of a substance when there is present in human body a substance or cell which have a functional antagonism, or the receptor being a receptor of substance A when there is present in human body a cell or substance which have a functional antagonism to cells on which the substance A causes some effects, may be found in many receptors, such as Calcitonin receptors (osteoclasts on which calcitonin acts shows functional antagonism to osteoblasts), glucagon receptors (glucogan having functional antagonism to insulin), somatostatin receptors (somotostatin having functional antagonism to growth hormones), and parathyroid hormone (the hormone having functional antagonism to calcitonin, etc.) and the like. Such receptors include but are not limited to 7-transmembrane type receptors such as Carcitonin receptors.

According to one method of the present invention, the amino acid sequences or the sizes of such receptors are analyzed to find receptors having different sizes and yet being identical receptors. This process may be performed by identifying a plurality of times the amino acid sequences or the sizes of the identified receptors, or by making use of literature if reported therein. Some examples of receptors, wherein there are receptors having two or more types having different sizes while being identical receptors may be found in calcitonin receptors, glucagon receptors, somatostain receptors, and the like.

After identifying that there are two or more types of receptors having different sizes for identical receptors, the amino acid sequences of these two or more types of receptors are compared with each other to identify which domain in the receptor of longer size is missing and thereby rendering it the receptor of shorter size. The missing domain in the receptor of shorter size is the physiologically active substance having some effects on the functional antagonism. In another words, some of the elements in the spliced structure are the physiologically active substances. It may be concluded that a physiologically active substance is bound to a receptor whereby some portion of the receptor is spliced and this spliced piece of the receptor shows some physiological activity, such as a controlling effect on the functional antagonism. It was confirmed, for example, that, as shown in the examples below, the missing domain in a calitonin receptor is bound to a receptor present on a osteoblast thereby promoting osteogenesis.

Since the missing domain identification by the above-described method has physiological activities, a physiologically active substance may be obtained by producing such domain. In most cases, the missing domain comprises peptides of relatively short sizes, and therefore, in such cases, a commercially available peptide synthesizer may be used to easily produce chemically synthesizing the physiologically active substances. Alternatively, such substances may be produced by using a method of gene engineering type according to known methods.

The physiological activity of the physiologically active substance thus obtained is related to the above-mentioned functional antagonism, and therefore, the activity can be easily confirmed by any of suitable methods applicable depending on each functional antagonism.

It is well-known to those skilled in the Art that, in peptides having physiological activities in general, the physiological activity thereof may be maintained even when some of the amino acids thereof are substituted by other amino acids, or when some amino acids are added, or when some of the amino acids are missing. Therefore, the present invention includes a method for producing a substance which has physiological activities inherent to physiologically active substances comprising the said missing domain, wherein some of the amino acids constituting the missing domain are replaced with other amino acids, or some other amino acids are added to amino acids constituting the missing domain, or some of the amino acids are missing from the amino acids constituting the missing domain. (Foregoing substance is referred to hereinafter in the present application as "derivative" of the missing domain.) Such a derivative preferably has not less than 70%, and more preferably 90%, of homogeneity with the above-mentioned missing domain.

EXAMPLES

The present invention is more specifically described below with reference to examples. It should be noted, however, that the present invention is not limited to the following examples.

Example 1

Identification of the Missing Domain of Calcitonin Receptor

The amino acid sequences of calcitonin receptors are described in Journal of Clinical Investigation, Vol. 90, No. 5 (1992). When the described amino acid sequences of calcitonin receptors described in the above reference are compared, the amino acids at $175^{th}$ through $190^{th}$ sequence positions of the amino acid sequence of the longer receptor are missing in the amino acid sequence of the shorter receptor. The amino acid sequence of the missing domain is shown in Sequence 1.

Example 2

Production of Peptides

By using a commercially available peptide synthesizer, a peptide having the amino acid sequence shown in Sequence 1 was synthesized.

Example 3

Proliferation Promotion of Osteoblasts

ROS cells from a rat, which are osteoblasts, (available from ATCC) were cultured in F10 growth medium containing 10% fetal bovine serum (available from Dainippon Pharmaceutical), and incubated in a chamber of constant temperature of 37° C. under humidified air containing 5% of $CO2$ gas. Using tryspin treatment, the cells were disseminated into a 24-well culture plate at the rate of $1\times105$ cells/well, and when the colonies became confluent, the medium was replaced with F10 medium having 1% of fetal bovine serum and were cultured for 24 hours. Then the peptide of the present invention produced in Example 2 was dissolved into F10 medium having 1% of fetal bovine serum, which was added to the wells at varying quantities, and the culturing was continued for additional 24 hours. After the culturing, the effect of promotion of cell proliferation by the peptide was measured by using MTT assay to determine the level of proliferation promotion effect as compared to the samples without any treatment. In this case, MTT assay and the calculation of proliferation promotion ratio were performed as follows: according to the protocol of MTF-Cell-Growth Assay kit commercially available from Funakoshi, Co., Ltd., the substance of the present invention was added to the wells at varying quantities and then it was left for one day and night, followed by counting by using colorimetry the number of living cells, making use of phenomena where cleavage of MTT (3-4,5 Dimethylthiazol-2YL) -2,5 Diphenyl Tetrazolium bromide to dark blue formazan by enzymes present in the mitochondria of a living cell. The following results in colorimetric value were obtained by adding varying quantities of the substance of the present invention, while the value for the control group to which no substance of the present invention is added being at 100%. The results are shown in Table 1, below.

TABLE 1

| Peptide added (μg/well) | Rate of proliferation promotion (%) |
|---|---|
| 0 | 100.0 |
| 0.001 | 109.6 |
| 0.01 | 110.5 |
| 0.1 | 636.2 |
| 1.0 | 1317.1 |

As can be seen from Table 1, the peptide identified according to the method of the present invention was confirmed to cause effects in promoting the proliferation for osteoblasts. Thus the peptide of the present invention is thought to cause a increase in bone density, and thus may be useful in the treatment of osteopathy, such as osteoporosis and the like.

Example 4

Presence on Osteoblasts of the Receptors of the Peptides of the Present Invention The peptides of the present invention was found to have promotional effect of proliferation of osteoblasts, whereby it is estimated that osteoblasts have receptors of the peptides of the present invention. If the receptors are present, the peptide of the present invention may be thought to be a fundamental substance for life, and therefore, it was investigated whether there are receptors on osteoblasts.

The peptide obtained in Example 2 was labeled with biotin, and the peptide of the present invention labeled to a predetermined quantity was added to ROS cells cultured in a similar method as in Example 3, followed by dissolving, to effectuate a competitive reaction, into F10 medium having 10% of fetal bovine serum the peptide of the present invention not labeled and thereafter by adding while the quantity is varied to observe the competitive reaction. The foregoing experimental operation was performed more specifically as follows: the peptide of the present invention was biotinated according to the protocol of Protein Biotin-Labeling kiet from SUMILON Co., and a predetermined quantity of the biotinated peptide was added to a predetermined number of cells disseminated in wells, followed by adding 0–0.512 μg/well of non-labeled peptide was added to each well to effectuate a competitive reaction for 6 hours, and thereafter, the cells were rinsed with PBS and the biotinated peptides bound to receptors of the cell surface was reacted with peroxidase labeled by streptoadipin to observe a color development reaction. When any receptor of the peptides of the present invention is present on the cell surface, a competitive reaction with the peptides of the present invention which are not labeled is effected and the color intensity is decreased. The results are shown in Table 2 below:

TABLE 2

| Added amount of Peptides of Non-labeled type (μg/well) | Ratio to added amount of peptides of labeled type (%) |
|---|---|
| 0 | 100 |
| 0.032 | 98.4 |
| 0.064 | 86.5 |
| 0.128 | 79.6 |
| 0.256 | 34.1 |
| 0.512 | 29.5 |

As shown in Table 2, the ratio to the added amount of peptides of labeled type varies depending on the added amount of the peptides on non-labeled type, and therefore, it is obvious that the osteoblasts have receptors for the peptide of the present invention and it is implied that the substance of the present invention plays a fundamental role.

[Acute Toxicity Test]

An acute toxicity test of the peptide produced in Example 2 was performed by using ddy male mice (weight 40–45 grams). The peptide of the present invention was dissolved into a saline solution (ph 6.0) to administer the solution through the caudal vein, and thereafter, the mice were subjected to observation for 14 days. The dosage was set at 1, 10, and 100 μg/kg. The results are shown in Table 3 below:

TABLE 3

| Dosage (μg/well) | Mortality |
|---|---|
| 1 | 0/5 |
| 10 | 0/5 |
| 100 | 0/5 |

Example 5

Identification of the Missing Domain in Glucagon Receptors

Using the same methodology as in Example 1, the amino acid sequences of Glucagon receptors described in FEBS Letters 351 (1994), pp. 271–275, were compared to identify the amino acid sequence of the domain being present in the receptors of longer size but missing in the receptors of shorter size. The amino acid sequence of the missing domain thus identified is shown in Sequence 2.

Example 6

Identification of the Missing Domain in Somatostatin Receptors

Using the same methodology as in Example 1, the amino acid sequences of Somatostatin receptors described in Molecular Pharmacology, 44: pp. 1008–1015 (1993), were compared to identify the amino acid sequence in the domain being present in the receptors of longer size but missing in the receptors of shorter size. The amino acid sequence of the missing domain thus identified is shown in Sequence 3.

What is claimed is:

1. A method of identifying a peptide as a receptor agonist or antagonist, said method comprising the steps of:

identifying a receptor that naturally occurs in two or more forms differing from one another in the length of their respective amino acid sequences, said differing receptor forms being receptive of a common ligand and being alternate products of a common gene;

identifying a domain that is present in the amino acid sequence of a larger form of said receptor but absent from the amino acid sequence of a smaller form of said receptor;

synthesizing a peptide consisting of the amino acid sequence of said domain; and testing said peptide for agonistic or antagonistic activity towards said receptor or said common ligand.

2. The method according to claim 1, wherein: the receptors are receptors of the 7-transmembrane type.

* * * * *